United States Patent [19]

Eijsbouts et al.

[11] Patent Number: 5,675,044
[45] Date of Patent: Oct. 7, 1997

[54] PROCESS FOR RECOVERY OF BISPHENOL-A FROM THERMOPLASTIC POLYMER CONTAINING DIHYDRIC PHENOL UNITS

[75] Inventors: Paul Eijsbouts, Hertogenbosch; Jos De Heer, Tholen; Gabrie Hoogland; Srikanth Nanguneri, both of Bergen op Zoom; Gert De Wit, Ossendrecht, all of Netherlands

[73] Assignee: General Electric Company, Pittsfield, Mass.

[21] Appl. No.: 673,990

[22] Filed: Jul. 1, 1996

[51] Int. Cl.$^6$ .................................................. C07C 37/84
[52] U.S. Cl. .......................... 568/724; 568/723; 568/722
[58] Field of Search ........................... 568/722, 723, 568/724

[56] References Cited

U.S. PATENT DOCUMENTS

| | | | |
|---|---|---|---|
| 4,242,527 | 12/1980 | Mark et al. | 568/724 |
| 4,885,407 | 12/1989 | Fox | 568/724 |
| 5,059,721 | 10/1991 | Powell et al. | 568/724 |
| 5,300,699 | 4/1994 | Furukawa et al. | 568/724 |
| 5,382,708 | 1/1995 | Kissinger . | |

OTHER PUBLICATIONS

The Merck Index; 11th Edition;#1815;p. 274 1989.

*Primary Examiner*—C. Warren Ivy
*Assistant Examiner*—Sreeni Padmanabhan

[57] ABSTRACT

A method of recovering dihydric phenol, particularly bisphenol-A, from compositions containing the reaction residue of bisphenol-A units which method comprises:

a. granulating a bisphenol-A containing polymer;
b. treating the particles with an alcohol, or any other organic swelling solvent miscible with water and easily distilled off from an aqueous solution, preferably a $C_1$–$C_{10}$ alcohol for a time sufficient to swell the particles;
c. contacting the swelled particles with a ammoniacal solution at a temperature of at least about 25° C. depending on the swelling solvent employed in order to selectively sever the ester bonds of the bisphenol-A residue units;
d. separating the liquid phase from the solid phase;
e. distilling ammonia and swelling solvent from the liquid phase of d. above, thus obtaining an essentially aqueous solution with dissolved urea and partially precipitated bisphenol-A;
f. adding sufficient water to the residue of e. above to precipitate bisphenol-A thereby forming a liquid and solid phase;
g. recovering the solid phase of bisphenol-A; and
h. drying the bisphenol-A.

Since urea is soluble in water, urea goes into solution in step f. above. The urea is, therefore, recoverable, as well, which can be used as such or broken down into its component parts such as carbon dioxide and ammonia which ammonia can also be reused in this ammonical process.

13 Claims, 1 Drawing Sheet

PROCESS FOR RECOVERY OF BISPHENOL-A FROM THERMOPLASTIC POLYMER CONTAINING DIHYDRIC PHENOL UNITS

FIELD OF THE INVENTION

This invention is related to a process for the recovery of dihydric phenol from a composition containing a thermoplastic polymer having the reaction residue of dihydric phenol units in its structure particularly polyesters including blends thereof with other materials. More specifically, the instant invention is related to recovery of bisphenol-A from polyesters for recycling thereof to produce products therefrom by an effective and potentially commercial process for such recovery.

BACKGROUND OF THE INVENTION

With the advent of manufactured materials, particularly thermoplastic materials, the problem of dealing with abandoned thermoplastic products and materials has been an increasing problem. Many plastics are not substantially biodegradable. Steps have been taken and are continuing to be taken to recycle plastic products. Unfortunately, recycling involves thermal processing of the thermoplastic and as such generally results in degradation of the thermoplastic both with respect to its chemical and physical properties thereby affecting its performance compared to virgin material. Each time a plastic is exposed to thermal processing, the properties thereof can become degraded such as impact resistance, deformation under load and temperature, tensile strength, flexural strength, elongation, flow behavior, etc. As more and more thermoplastic resins are employed in preparing consumer products, the plastic scrap dilemma becomes ever increasing. Clearly, a method of recovering scrap plastics and converting them into useful chemical constituents would be an asset to the public and the plastics industry.

U.S. Pat. 4,885,407 describes a process of recovering a dihydric phenol from scrap or otherwise abandoned aromatic polyesters such as polycarbonates. The process involves contacting the polycarbonate with an aqueous ammoniacal solution and a solvent for the polycarbonate such as methylene chloride to form two liquid phases, with the top phase being aqueous and the bottom phase being methylene chloride phase. The phases are separated and the methylene chloride evaporated from the liquid phase. Obviously, methylene chloride presents environmental issues.

SUMMARY OF THE INVENTION

It has now been surprisingly discovered and in accordance with the instant invention, a process has been developed to effectively separate and selectively sever the ester bonds of an aromatic polyester such as a polycarbonate, a copolyester carbonate, a polyarylate, and the like. Briefly, the process involves contacting the aromatic polycarbonate, for example, with an organic swelling agent such as methanol for a period of time and then adding an aqueous ammoniacal solution. The ammoniacal solution is of sufficient strength to selectively sever the ester bond of the polycarbonate and to form the ammonium salt of bisphenol-A (ammonium phenolate) which is soluble in the aqueous phase. A two phase system is formed, namely a solid phase and a liquid phase of which the liquid phase contains both urea and the ammonium salt of bisphenol-A. Separation of the phases is achieved by filtration. The solid phase contains other materials such as fillers, pigments, reinforcing agents, other polymeric materials such as acrylonitrile-butadiene-styrene (ABS), polybutylene terephthalate (PBT), and the like. From this liquid phase, the low boiling methanol and excess ammonia are distilled off. This leaves urea dissolved in water and partially separated bisphenol-A by precipitation. Sufficient water is added until all of the bisphenol-A is precipitated out of the solution and removed by filtration. The solid bisphenol-A is then dried, may be purified and ready for use as an intermediate in chemical reactions.

DETAILED DESCRIPTION OF THE INVENTION

Figure 1:
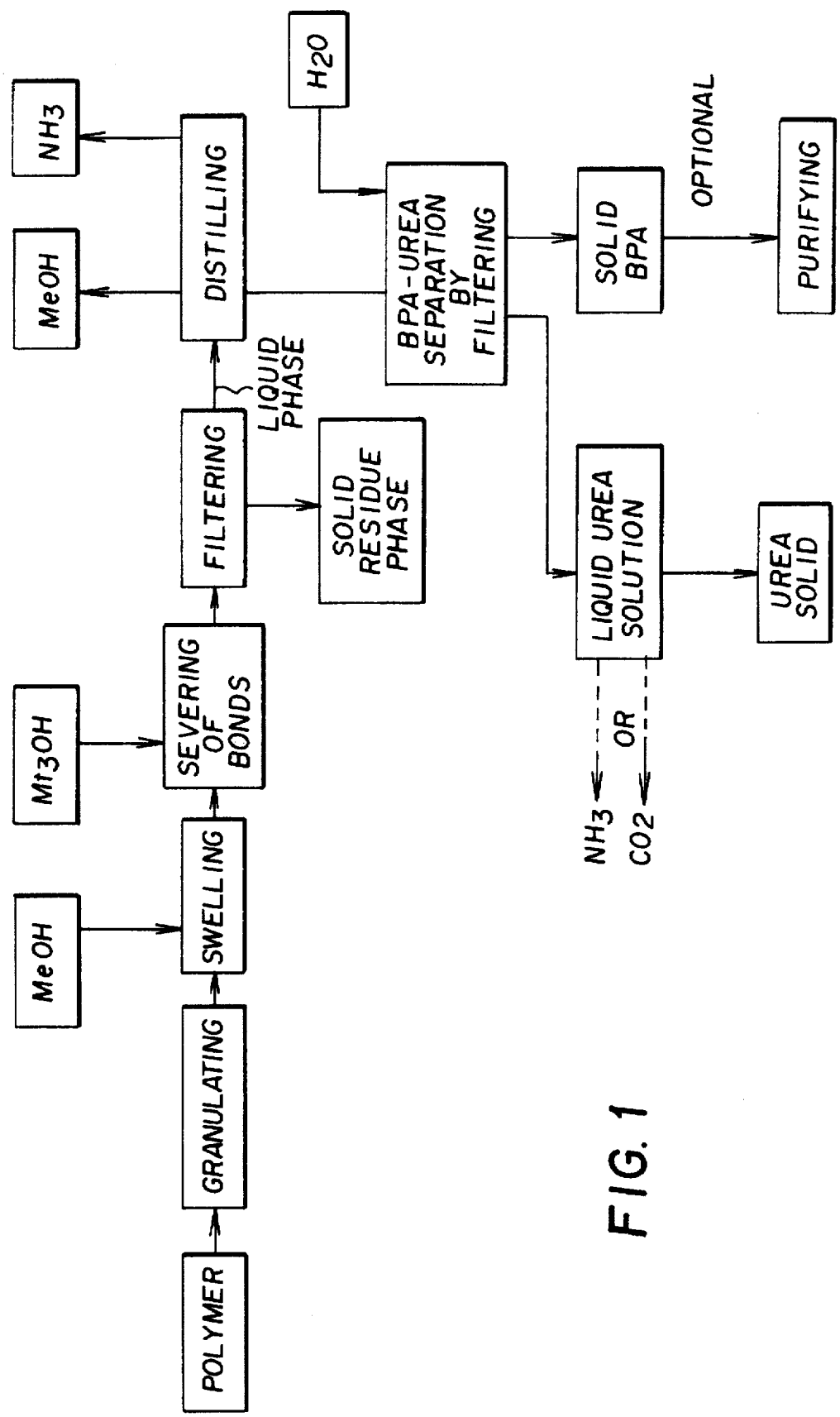

This invention is directed to a novel process of recovering dihydric phenol, particularly bisphenol-A, from a composition containing a thermoplastic polymer having the reaction residue of dihydric phenol units in its polymer structure. Such thermoplastics preferably include polyesters or blends of polyesters with other materials which polyesters contain the reaction residue of dihydric phenol units in its polymer structure. The process of this invention comprises:

(a) Granulating a composition containing a thermoplastic polymer having in its structure the reaction residue of dihydric phenol units;

(b) Treating the granulated particles with an organic swelling solvent that is miscible with water and is easily distilled off from an aqueous solution and for a time sufficient to swell the particles;

(c) Contacting the swelled particles with an aqueous ammoniacal solution of sufficient strength to selectively sever the ester bonds of the dihydric phenol units in the thermoplastic polymer and at a temperature of at least about 25° C., thereby forming a solid and a liquid phase;

(d) Separating the liquid phase from the solid phase;

(e) Distilling ammonia and the organic swelling solvent from the liquid phase of (d);

(f) Adding sufficient water to the residue of (e), which contains dissolved urea and partially precipitated dihydric phenol, to precipitate dihydric phenol thereby forming a liquid and a solid phase, which is dihydric phenol;

(g) Separating the solid phase from the liquid phase; and (h) Drying the dihydric phenol precipitate of (g).

Swelling of the polymer particles in this invention is essentially free of dissolving the particles and increases the free volume of the particles. For example, alcohol does not dissolve a dihydric phenol such as a polycarbonate. The recovered dihydric phenol, disclosed above, may be subjected to further purification by such means as distillation, recrystallization in a solvent, vacuum distillation, activated charcoal adsorption, or other purification processes.

In the practice of this invention, the aqueous liquid phase of step (f) above contains dissolved urea which urea can then be recovered from the aqueous solution thereof. Alternatively, the recovered urea can be purified or separated into its component parts, namely, ammonia and carbon dioxide both of which or the urea itself have commercial use in the chemical industry.

Granulating the thermoplastic articles to a particular size is not critical to the ammonolysis chemistry of this invention. However, it is preferable that the average particles size of the granulated material be about 0.2 to about 10 mm in order to provide greater surface area exposure to the organic swelling solvent in the swelling phase of the instant invention. Generally, the finer the granulation, the shorter the swell time and subsequent reaction time for a desired yield of dihydric phenol. The preferred size of the particles during granulation of the thermoplastic material can also be a function of the composition. Even in compositions that are predominately polycarbonate, particle size has a favorable influence on the swell and reaction time. Obviously, the finer the particle size, the more efficient is the swell phenomena and reaction time. However, if the composition is a blend of a polycarbonate and other materials such as other polymers not containing the reaction residue of dihydric phenol units, a finer granulation will influence the swell and reaction time, as well as the efficiency of the reaction by providing greater surface area due to the finer granulation.

The time of treating of the particles with the organic swelling solvent in the swelling step of the process can vary depending on particle size and composition of the thermoplastic material. The swelling time should be sufficient to swell the particles and preferably may vary from about 10 minutes or less to about 60 minutes or more. The organic swelling solvent may be any organic swelling solvent that is miscible with water and is distilled off from an aqueous solution. Preferably, the organic swelling solvent may be either an alcohol, a ketone or a mixture thereof if they are miscible. The alcohol can be any alcohol that will swell the thermoplastic particles and is preferably an alcohol of $C_1$–$C_{10}$ carbon, with the preferred alcohol being methanol. Other alcohols included herein are ethanol, propanol, isopropanol, butanol, and the like, including other organic alcohols. In addition, the other preferred organic swelling solvent is any ketone, but is preferably acetone, methyl ethyl ketone, isopropyl ketone and the like.

Following the swelling step, sufficient aqueous ammoniacal solution is then added in order to selectively sever the ester bonds of the dihydric phenol units in, preferably, a relatively short period of time, i.e., for example, the polycarbonate bonds in the thermoplastic material. The strength of the aqueous ammoniacal solution, i.e., ammonium hydroxide, is generally concentrated ammonium hydroxide having a molarity of about 18, but can be a lower molarity such as about 7 or lower. However, the lower the concentration of ammoniacal solution, the longer is the contact time for a desired yield of dihydric phenol. Preferably, a suitable molar range of ammonium hydroxide to thermoplastic polymer should be in the range of about 4.0 to about 25 times, and more particularly about 5 to about 25 times. It should be understood, however, that higher and lower molarity ammonium hydroxide can also be employed. In this process step, two phases are formed, a solid phase and a liquid phase.

The solid phase is then separated from the liquid phase. The liquid phase contains urea, water, methanol and the ammonium salt of bisphenol-A (dihydric phenolate ammonium salt). This liquid phase is then distilled to remove methanol and excess ammonia. Upon distillation of ammonia, the ammonium salt of bisphenol-A (BPA) transfers or converts to BPA. This leaves an aqueous solution of urea and partially precipitated bisphenol-A. Sufficient water is then added to the acqueous solution to maximize the precipitation of bisphenol-A. Separation of the two phases is accomplished by simple filtration. The solid bisphenol-A is dried and is usually in powder form. The recovered bisphenol-A may be purified and is available for use as a reactant in chemical reactions particularly for producing aromatic polycarbonates, epoxies, polyarylates and such other products in which bisphenol-A is a reactant.

FIG. 1 is a flow diagram of the process of this invention showing the procedure hereof to obtain solid BPA. The BPA recovered is crude BPA, but may be purified.

The polymeric materials that can be employed in the recovery process are those polymeric materials which are prepared using as one of the reactants a dihydric phenol to form a polymer include, but are not limited thereto, an aromatic polycarbonate, an aromatic copolyester carbonate, a polyarylate or mixtures thereof or mixtures thereof with other materials and/or polymers. Such other materials may include either polymers such as nylon, polybutyleneterephthalate, polyethylene terephthalate, polyphenylene ether, acrylonitrile-butadiene-styrene (ABS), and the like. Other materials include fillers (glass, carbon, mineral, etc.), pigments, rubber (natural or synthetic), impact modifiers, reinforcing agents, other than fillers, etc. These materials are separable from the polymer containing the dihydric phenol residue units in this process.

It should be noted that the form of the dihydric phenol in the liquid phase is believed to be an ionic complex of ammonium hydroxide and bisphenol-A because the solution exhibits ionic conductivity. This is supported by an increase in measured ionic conductivity as a function of reaction time. Also, the formation of the ammonium salt of bisphenol-A has been further confirmed by infrared analysis.

It should also be understood that the term "scrap polyester" containing dihydric phenol residue units is not limited to so-called scrap material. It can include material other than "scrap" such as abandonded virgin resin not converted by molding and which can be subjected to the process of this invention and the depolymerization thereof resulting in recovered bisphenol-A.

In the practice of this invention, other constituents of the material may also be recovered for recycling such as other polymers. For example, a blend of polycarbonate and PBT when subjected to the instant process results in recovery of PBT for recycling purposes. This is also applicable to other blends where the blends contain dihydric phenol units, the ester units of which can be selectively severed by this process with the other parts of the blend being recoverable.

The following examples are intended to illustrate this invention and are not intended to limit or narrow the inventive concept disclosed herein.

EXAMPLE 1

A clear section of a polycarbonate sheet (essentially 99 weight % polycarbonate) was granulated in a laboratory grinder. The granulated material had an average particle size of about 3 mm.

To about 10.5 grams of the granulated polycarbonate in a laboratory beaker, 45 ml of methanol (100%) was added. The mixture was stirred at room temperature for about 60 minutes. The polycarbonate particles were observed to swell effectively in methanol. About 45 ml of a 25% by weight aqueous ammonium hydroxide solution (a 50:50 weight ratio of ammonium hydroxide to methanol) was added to the swollen particles-methanol mixture and agitated for about 1 hour at a temperature of about 40° C. Two phases were formed consisting of a solid phase and a liquid phase. The phases were separated by filtration and the solid phase was dried and weighed. It was determined that the solid phase was about 1 weight % (0.1 g) of the weight of the total polycarbonate sample.

The liquid phase was then distilled to remove ammonia and methanol during which the ammonium salt of the dihydric phenolate was converted to the dihydric phenol form of bisphenol-A. The residue was a solid consisting of urea and bisphenol-A since upon distillation, the ammonium salt of bisphenol-A was transferred or converted to bisphenol-A. Sufficient water was added to the essentially aqueous solution of dissolved urea and partically precipitated hisphenol-A to completely separate the bisphenol-A from the urea liquid phase. Since urea is soluble in water, two phases were formed, a solid phase which was bisphenol-A since it is insoluble in water and a liquid phase which was an aqueous solution of urea. The bisphenol was recovered by filtration, dried, weighed and purified through activated charcoal adsorption.

The visual color of the bisphenol-A was white. It was determined that the bisphenol-A recovered (9.3 g) was about 99 weight % of the bisphenol-A in the original polycarbonate sample. It was also determined that the yield of urea is about 96 weight %.

EXAMPLE 2

Example 1 was repeated except that about 11.2 grams of a blend of about 69 weight % of polycarbonate and about 31 weight % of polybutylene terephthalate and other additives was employed herein instead of the sample employed in Example 1, and except that the reaction time, i.e., the mixing time of the methanol treated sample with the aqueous ammonium hydroxide and methanol solution was about six hours. The solid phase recovered from the reaction (3.62 g) was about 33 weight % of the initial sample.

The visual color of the recovered purified bisphenol-A was white. The bisphenol-A recovered was about 99 weight % of the bisphenol-A employed in the original sample. The polybutylene terephthalate recovered from the solids after reaction with ammonium hydroxide and separation was about 99 weight % of the polybutylene terephthalate in the initial sample. Also, it was determined that the yield of urea was about 86.5 weight %.

EXAMPLE 3

Example 1 was again repeated except that the sample employed in place thereof was a blend of about 59 weight % of polycarbonate and about 11 weight % of ABS and other additives. The reaction time, i.e., the mixing time of the methanol treated sample with aqueous ammonium hydroxide and methanol solution was for a period of about three hours. The solid phase recovered from the reaction was about 42 weight % of the initial sample.

The visual color of the recovered sample of bisphenol-A was whitish brown. The bisphenol-A recovered was about 95 weight % of the bisphenol-A employed in the initial sample. The ABS recovered was about 99 weight % of the ABS in the initial sample. The yield of urea was determined to be about 87 weight %.

While the invention has been described and illustrated in connection with certain preferred embodiments thereof, it will be apparent to those skilled in the art that the invention is not limited thereto. Accordingly, it is intended that the appended claims cover all modifications which are within the spirit and scope of this invention.

What is claimed is:

1. A method of recovering a dihydric phenol from a composition containing a thermoplastic polymer having the reaction residue of dihydric phenol units in its polymer structure, which method comprises:

a. granulating a composition containing a thermoplastic polymer having the reaction residue of dihydric phenol units in its polymer structure;

b. treating the granulated particles of the thermoplastic composition with an organic swelling solvent that is miscible with water and is easily distilled off from an aqueous solution and for a time sufficient to swell the particles;

c. contacting the swelled granulated particles with an aqueous ammoniacal solution of sufficient molar strength to selectively sever the ester bonds of the reaction residue of the dihydric phenol units in the thermoplastic polymer and at a temperature of at least about 25° C., thereby forming a solid phase and a liquid phase;

d. separating the liquid phase from the solid phase;

e. distilling the ammonia and the organic swelling solvent from the liquid phase;

f. adding sufficient water to the residue of e. which contains dissolved urea and partially precipitated dihydric phenol to precipitate dihydric phenol thereby forming a liquid and a solid phase of dihydric phenol; and g. separating the insoluble solid dihydric phenol portion from the liquid phase.

2. The method of claim 1 wherein the granulated particle size has an average particle size of about 2 to about 25 mm.

3. The method of claim 1 wherein the organic swelling solvent is an alcohol of $C_1$–$C_{10}$ carbon.

4. The method of claim 3 wherein the alcohol is methanol.

5. The method of claim 1 wherein the organic swelling solvent is a ketone.

6. The method of claim 5 wherein the ketone is acetone.

7. The method of claim 1 wherein the contacting of the swelled granulated particles with the aqueous ammoniacal solution is at a temperature of about 30° C. to about 50° C.

8. The method of claim 1 wherein the liquid phase of step f. is a solution of urea.

9. The method of claim 8 wherein urea is recovered from the solution by the process of vacuum distillation to remove water.

10. The method of claim 1 wherein the recovered dihydric phenol is purified by charcoal adsorption.

11. The method of claim 1 wherein the composition contains polymers selected from the group consisting essentially of polycarbonates, copolyestercarbonates, polyarylates, blends thereof and blends with other polymers.

12. The method of claim 1 wherein the dihydric phenol recovered from the method thereof is bisphenol-A.

13. A polycarbonate prepared from the bisphenol-A obtained by the method of claim 10.

* * * * *